United States Patent [19]

Jaeggi et al.

[11] 3,978,041
[45] Aug. 31, 1976

[54] PHENOXY SUBSTITUTED GLYCOSIDES

[75] Inventors: Knut A. Jaeggi, Basel; Herbert Schröter, Fullinsdorf; Franz Ostermayer, Riehen, all of Switzerland

[73] Assignee: Ciba-Geigy Corporation, Ardsley, N.Y.

[22] Filed: Feb. 3, 1975

[21] Appl. No.: 546,648

Related U.S. Application Data

[63] Continuation-in-part of Ser. No. 421,558, Dec. 4, 1973, abandoned.

[30] Foreign Application Priority Data

Dec. 22, 1972 Switzerland.................. 18731/72
Oct. 24, 1973 Switzerland.................. 15022/73
Feb. 8, 1974 Switzerland.................. 1775/74

[52] U.S. Cl.................................. 536/4; 424/180; 536/119
[51] Int. Cl.². ........................................ C07H 15/00
[58] Field of Search.................. 260/210 R, 209

[56] References Cited
UNITED STATES PATENTS 2,252,725  8/1941  Niederl ...................... 260/210 R
3,152,115  10/1964  Morel et al. ................ 260/210 R

*Primary Examiner*—Johnnie R. Brown
*Attorney, Agent, or Firm*—Joseph G. Kolodny; John J. Maitner; Theodore O. Groeger

[57] ABSTRACT

1-Phenoxy-2-hydroxy-3-amino-propanes of the formula I

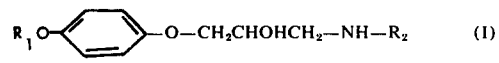

wherein $R_1$ is a sugar residue and $R_2$ is isopropyl, tert.-butyl or α-methyl-phenethyl optionally substituted in the phenyl part, and the salts thereof are useful as positively inotropic agents, especially in the treatment of insufficiency of the cardiac muscle.

11 Claims, No Drawings

PHENOXY SUBSTITUTED GLYCOSIDES

This is a continuation-in-part of our application Ser. No. 421,558 filed Dec. 4, 1973, now abandoned.

The invention relates to new 1-phenoxy-2-hydroxy-3-amino-propanes of the formula I

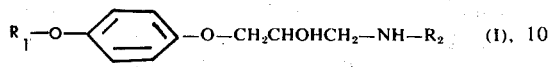 (I)

wherein $R_1$ is a sugar residue and $R_2$ is isopropyl, tert.-butyl or α-methyl-phenethyl or 1-methyl-3-phenylpropyl which are optionally substituted in the phenyl part, and to processes for their manufacture.

A sugar residue $R_1$ is, for example, a pentosidyl residue or a hexosidyl residue, especially an aldopentosidyl residue or an aldohexosidyl residue, preferably a 1-aldopentosidyl residue or a 1-aldohexosidyl residue. By way of example, the 1-glucopyranosidyl residue may be singled out. A sugar residue can also contain protective groups or substituted hydroxyl groups.

As protective groups there are in particular to be understood those substituted hydroxyl groups which can be converted into free hydroxyl groups, for example as described below.

Substituted hydroxyl groups are, in particular, etherified or esterified hydroxyl groups.

Etherified hydroxyl groups are, for example, aliphatically or araliphatically etherified hydroxyl, such as lower alkoxy, for example those with up to 7 and in particular with up to 4 C atoms, such as ethoxy and especially methoxy or n-propoxy, or phenyl-lower alkoxy optionally substituted in the phenyl part, wherein the lower alkoxy part in particular corresponds to the above lower alkoxy and is preferably methyleneoxy and wherein examples of substituents which may be mentioned are lower alkyl such as lower alkyl with up to 7, in particular with up to 4, C atoms, such as i- or n-propyl, ethyl or especially methyl, lower alkoxy, such as mentioned above, trifluoromethyl and especially halogen, such as bromine and above all chlorine, as well as lower alkylbenzyl, for example methylbenzyl, lower alkoxybenzyl, for example methoxybenzyl, trifluoromethylbenzyl or in particular benzyl or halogenobenzyl, for example chlorobenzyl.

Etherified hydroxyl groups, for example also include those in which two adjacent or sterically adjacent hydroxyl groups are together replaced by an ylidenedioxy radical. Ylidenedioxy is, in particular, lower alkylidenedioxy, such as lower alkylidenedioxy with up to 7, above all with up to 4 C atoms, such as, in particular, isopropylidenedioxy or optionally substituted benzylidenedioxy, such as benzylidenedioxy substituted by lower alkyl, lower alkoxy or halogen, for example methylbenzylidenedioxy, methoxybenzylidenedioxy or chlorobenzylidenedioxy and especially benzylidenedioxy.

Esterified hydroxyl groups are, for example, lower alkanoyloxy, for example with up to 7, especially with up to 4, C atoms, such as propionyloxy or especially acetoxy, or optionally substituted benzoyloxy, wherein examples of substituents which may be mentioned are lower alkyl, such as mentioned above, lower alkoxy, such as mentioned above, or halogen, such as mentioned above, such as methylbenzoyl, methoxybenzoyl, chlorobenzoyl or especially benzoyl.

α-Methylphenethyl or 1-methyl-3-phenyl-propyl $R_2$ optionally substituted in the phenyl part is, for example, α-methylphenethyl or 1-methyl-3-phenyl-propyl substituted in the phenyl part by hydroxyl or lower alkoxy. Lower alkoxy is therein in particular lower alkoxy with up to 7 C atoms, above all with up to 4 C atoms, such as ethoxy, n- or iso-propoxy, n-, sec.- or tert.-butoxy or above all methoxy. Thus, α-methylphenethyl optionally substituted in the phenyl part is, for example, o-, m- or p-hydroxy-α-methyl-phenethyl, o-, m- or p-methoxy-α-methyl-phenethyl and above all α-methylphenethyl unsubstituted in the phenyl part. Equally, 1-methyl-3-phenyl-propyl optionally substituted in the phenyl part is, for example 1-methyl-3-phenyl-propyl substituted in the phenyl part by hydroxyl or methoxy in the o-, m- or p-position, and above all 1-methyl-3-phenyl-propyl unsubstituted in the phenyl part.

The new compounds possess advantageous pharmacological properties. Thus they show a positively chronotropic and in particular a positively inotropic action, as can above all be demonstrated by an increase in the myocardiac contractibility (probably due to direct stimulation of the β-receptors) and of the pulse rate, for example as can be demonstrated on non-narcotised dogs by recording various contractibility parameters, such as maximum acceleration of the blood flow in the aorta and of the pulse rate on oral administration in doses of about 0.1 to about 10 mg/kg. The new compounds are therefore useful as positively inotropic agents, especially in the treatment of insufficiency of the cardiac muscle.

They are furthermore also useful as valuable intermediate products for the manufacture of other useful substances, especially of pharmaceutically active compounds.

Compounds to be singled out are 1-phenoxy-2-hydroxy-3-amino-propanes Ia of the formula I, wherein $R_1$ is optionally O-lower alkylated, O-aryl-lower alkylated, O-lower alkanoylated, O-benzoylated or O,O-ylideneylated 1-glucopyranosidyl and $R_2$ is isopropyl, tert.-butyl or α-methylphenethyl or 1-methyl-3-phenyl-propyl which are optionally substituted in the phenyl part.

Compounds to be particularly singled out are 1-phenoxy-2-hydroxy-3-amino-propanes Ib of the formula I, wherein $R_1$ is O-methyl-1-glucopyranosidyl, O-benzyl-1-glucopyranosidyl, O-chlorobenzyl-1-glucopyranosidyl, O-acetyl-1-glucopyranosidyl, O-benzoyl-1-glucopyranosidyl, 2,4-O-isopropylidene-1-glucopyranosidyl, 2,4-O-benzylidene-1-glucopyranosidyl or 1-glucopyranosidyl and $R_2$ is isopropyl, tert.-butyl or α-methylphenethyl or 1-methyl-3-phenylpropyl which are optionally substituted in the phenyl part by hydroxyl or lower alkoxy.

Above all there should be mentioned 1-phenoxy-2-hydroxy-3-amino-propanes Ic of the formula I, wherein $R_1$ is 1-glucopyranosidyl and $R_2$ is isopropyl or tert.-butyl.

Compounds to be singled out by name are in particular 1-[p-(β-D-glucopyranosidyloxy)-phenoxy]-2-hydroxy-3-isopropylamino-propane and 1-[p-(β-D-glucopyranosidyloxy)-phenoxy]-2-hydroxy-3-tert.-butylamino-propane.

Further compounds to be singled out are optically active 1-phenoxy-2-hydroxy-3-aminopropanes, having the S-configuration, of the formula I, wherein $R_1$ is optionally O-lower alkanoylated or O-benzoylated 1-glucopyranosidyl and $R_2$ is isopropyl, tert.-butyl or α-methyl-phenethyl or 1-methyl-3-phenyl-propyl which are optionally substituted in the phenyl part.

Compounds to be singled out particularly are optically active 1-phenoxy-2-hydroxy-3-aminopropanes, having the S-configuration, of the formula I, wherein $R_1$ is O-acetyl-1-glucopyranosidyl, O-benzoyl-1-glucopyranosidyl or 1-glucopyranosidyl and $R_2$ is isopropyl, tert.-butyl or α-methylphenethyl or 1-methyl-3-phenyl-propyl which are optionally substituted in the phenyl part by hydroxyl or lower alkoxy.

Compounds to be singled out very particularly are the optically active end products of the formula I having the S-configuration, manufactured according to the examples, and their salts, especially their therapeutically usable salts.

The new 1-phenoxy-2-hydroxy-3-amino-propanes of formula I can be manufactured according to methods which are in themselves known.

It is possible, for example, to react a compound of the formula IV

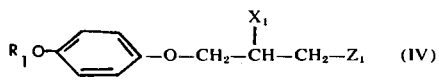

wherein $R_1$ has the above meaning, with a compound of the formula V $$Z_2 - R_2 \qquad (V)$$

wherein $R_2$ has the above meaning, one of the radicals $Z_1$ and $Z_2$ is amino and the other is reactive esterified hydroxyl and $X_1$ is hydroxyl, or $Z_1$ together with $X_1$ is epoxy and $Z_2$ is amino.

Reactive esterified hydroxyl is, in particular, a hydroxyl group esterified by a strong inorganic or organic acid, above all a hydrogen halide acid, such as hydrochloric acid, hydrobromic acid or hydriodic acid, or sulphuric acid or an organic sulphonic acid, such as an aromatic sulphonic acid, for example benzenesulphonic acid, 4-bromobenzenesulphonic acid or 4-toluenesulphonic acid. Thus, reactive esterified hydroxyl is, in particular, chlorine, bromine or iodine.

This reaction can be carried out in the usual manner. If a reactive ester of the formula IV or V is used, the reaction is preferably carried out in the presence of a basic condensation agent and/or with an excess of amine of the formula IV. Examples of suitable basic condensation agents are alkali metal hydroxides, such as sodium hydroxide or potassium hydroxide, alkali metal carbonates, such as potassium carbonate, and alkali metal alcoholates, such as alkali metal lower alkanolates, for example sodium methylate, potassium ethylate or potassium tertiary butylate.

The new optically active 1-phenoxy-2-hydroxy-3-amine-propanes of formula I having the S-configuration can be manufactured according to methods which are in themselves known.

It is possible, for instance to react a phenol of the formula VI

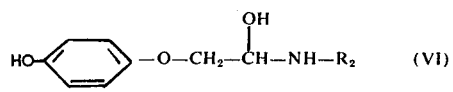

wherein $R_2$ has the above meaning, with a O-lower alkanoylated or O-benzoylated sugar, wherein lower alkanoyl corresponds to the definition given. The reaction is carried out in the presence of a suitable silyl compound which forms a reactive intermediate product with one of the reactants employed, which intermediate product then reacts further with the other reactant. Examples of silyl compounds which can be used are trimethylsilyl chloride or hexamethyldisilazane. The reaction medium used is an inert solvent, such as, say, a halogenated hydrocarbon, for example chloroform, carbon tetrachloride, dichloroethane, tetrachloroethane or chlorobenzene, or an aromatic solvent such as benzene or toluene, or mixtures of the abovementioned solvents. The reaction temperature lies within the limits of 20° to 150°C, especially 80° to 120°C.

In resulting compounds it is possible, within the definition of the end products, to modify, introduce or split off substituents in the usual manner; alternatively, resulting compounds can be converted into other end products in the customary manner.

Thus it is possible to split off the protective groups in resulting compounds which carry protective groups in the sugar residue $R_1$. For example it is possible, in resulting compounds in which one or more hydroxyl groups in the sugar residue are protected by an optionally substituted benzyl radical or in which two adjacent hydroxyl groups in the sugar residue $R_1$ are together protected by an optionally substituted benzylidene radical, to split off these radicals in the usual manner. Optionally substituted benzyl is, for example, halogenobenzyl, such as chlorobenzyl, lower alkylbenzyl, such as methylbenzyl or lower alkoxybenzyl, such as methoxybenzyl, and in particular unsubstituted benzyl. Optionally substituted benzylidene is, for example, halogenobenzylidene, such as chlorobenzylidene, lower alkylbenzylidene, such as methylbenzylidene, or lower alkoxybenzylidene such as methoxybenzylidene, and especially unsubstituted benzylidene. The splitting off can for example be effected by reduction, for example by treatment with catalytically activated hydrogen, such as hydrogen in the presence of a hydrogenation catalyst, for example platinum, palladium or Raney nickel, yielding corresponding compounds with free hydroxyl groups in the sugar residue $R_1$.

In resulting compounds in which one or more hydroxyl groups in the sugar residue $R_1$ are protected by acyl, the acyl radicals can be split off in the customary manner, for example by hydrolysis or by alcoholysis, preferably in the presence of a mild basic agent, such as an alkali metal bicarbonate, for example sodium bicarbonate, or ammonia dissolved in methanol, giving corresponding compounds with free hydroxyl groups in the sugar residue $R_1$.

The reactions mentioned can optionally be carried out simultaneously or successively and in optional sequence.

The reactions mentioned are carried out in the usual manner in the presence or absence of diluents, condensation agents and/or catalytic agents, at lowered, ordinary or elevated temperature and if appropriate in a closed vessel.

Depending on the process conditions and starting substances, the end products are obtained in the free form or in the form of their acid addition salts, which is also encompassed by the invention. Thus, for example, basic, neutral or mixed salts and where relevant also hemihydrates, monohydrates, sesquihydrates or polyhydrates thereof, can be obtained. The acid addition salts of the new compounds can be converted into the free compound in a manner which is in itself known, for example by means of basic agents, such as alkalis or ion exchangers. On the other hand, the resulting free bases can form salts with organic or inorganic acids. Acids used for the preparation of acid addition salts are in particular those which are suitable for forming therapeutically usable salts. As examples of such acids there may be mentioned, hydrogen halide acids, sulphuric acids, phosphoric acids, nitric acid and aliphatic, alicyclic, aromatic or heterocyclic carboxylic acids or sulphonic acids, such as formic acid, acetic acid, propionic acid, succinic acid, glycollic acid, lactic acid, malic acid, tartaric acid, citric acid, ascorbic acid, maleic acid or pyruvic acid, fumaric acid, benzoic acid, anthranilic acid, p-hydroxybenzoic acid, salicylic acid or embonic acid, methanesulphonic acid, ethanesulphonic acid, hydroxyethanesulphonic acid or ethylenesulphonic acid, halogenobenzenesulphonic acids, toluenesulphonic acid, cyclohexylaminesulphonic acid or sulphanilic acid.

These or other salts of the new compounds such as, for example, the picrates, can also serve for the purification of the resulting free bases by converting the free bases into salts, and isolating these and again liberating the bases from the salts. Because of the close relationships between the new compounds in the free form and in the form of their salts, the free compounds are, in the preceding and following text, where appropriate also to be understood to include the corresponding salts, with regard to general sense and intended use.

The invention also relates to those embodiments of the process according to which a compound obtainable as an intermediate product at any stage of the process is used as the starting product and the missing process steps are carried out, or the process is stopped at any stage, or in which a starting substance is formed under the reaction conditions or in which a reactant is present in the form of its salts, if appropriate.

The new compounds can, depending on the choice of the starting substances and procedures, be in the form of optical antipodes or racemates or, where they contain at least two asymmetrical carbon atoms, also in the form of isomer mixtures.

Resulting isomer mixtures can be separated into the two stereoisomeric (diastereomeric) pure racemates in a known manner on the basis of the physico-chemical differences of the constituents, for example by chromatography and/or fractional crystallisation.

Resulting racemates can be resolved into the diastereomers according to known methods, for example by recrystallisation from an optically active solvent, with the aid of micro-organisms or by reaction with an optically acitve acid which forms salts with the racemic compound and separation of the salts obtained in this manner, for example on the basis of their different solubilities, and the antipodes can be liberated from the diastereomers by treatment with suitable agents. Particularly customary optically active acids are, for example, the D- and L-forms of tartaric acid, di-o-toluyltartaric acid, malic acid, mandelic acid, camphorsulphonic acid or quinic acid. Advantageously, the more active of the two antipodes is isolated.

Preferably, the starting substances used for carrying out the reactions according to the invention are those which lead to the groups of end products which were particularly mentioned initially and especially to the end products which have been particularly described or singled out.

The starting substances are known or can, if they are new, be obtained according to methods which are in themselves known. Compounds IV can be prepared in the usual manner for a phenol by reaction with a reactive derivative of a propanol $HOCH_2—CHX_1—CH_2Z_1$, such as, for example, with epichlorohydrin.

The new compounds can be used as medicines, for example in the form of pharmaceutical preparations in which they or their salts are present as a mixture with a pharmaceutical, organic or inorganic, solid or liquid excipient which is suitable for, for example, enteral or parenteral administration. Suitable substances for forming the excipient are those which do not react with the new compounds such as, for example, water, gelatine, lactose, starch, magnesium stearate, talc, vegetable oils, benzyl alcohols, polyalkylene glycols or other known medicinal excipients. The pharmaceutical preparations can for example be in the form of tablets, dragees, capsules or suppositories or in a liquid form as solutions (for example as an elixir or syrup), suspensions or emulsions, They are optionally sterilised and/or contain auxiliaries, such as preservatives, stabilisers, wetting agents or emulsifiers, salts for regulating the osmotic pressure or buffers. The preparations, which can also be used in veterinary medicine, are obtained according to customary methods. The daily dose for a warm-blooded animal of about 75 kg body weight is about 10–100 mg, preferably about 20–40 mg.

The examples which follow explain the invention without however restricting it.

EXAMPLE 1

16.4 g (0.05 mol) of 4-(2,3-epoxy-propoxy)-phenyl-β-D-glucopyranoside and 11.8 g (0.20 mol) of isopropylamine are dissolved in 250 ml of methanol and heated for 5 hours under reflux. The mixture is then completely evaporated under a waterpump vacuum. The oily residue is dissolved in ethanol and 8.95 g (0.05 mol) of N-cyclohexylsulphamic acid, dissolved in isopropanol, are added. The reaction product which precipitates in a crystalline form is filtered off whilst excluding moisture. After recrystallisation from ethanol-isopropanol, 1-[p-(β-D-glucopyranosidyloxy)-phenoxy]-2-hydroxy-3-isopropylaminopropane-N-cyclohexyl sulphamate of melting point 70°–110°C is obtained, $[\alpha]_D^{20} = -28.8°$ in methanol.

The starting material can be obtained as follows:

27.2 g (0.1 mol) of hydroquinone-β-D-glucopyranoside and 250 ml of epichlorohydrin are dissolved in 1 liter of ethanol, 6.9 g (0.05 mol) of potassium carbonate are added and the mixture is heated for 6 hours under reflux. The precipitate which separates out is filtered off. The filtrate is evaporated in a waterpump vacuum. The residue is dissolved in hot ethanol and the solution is filtered. The filtrate is cooled and ether is added until the mixture begins to turn cloudy. The reaction product which hereupon precipitates as crystals is filtered off and washed with ether. 4-(2,3-Epoxypropoxy)-phenyl-β-D-glucopyranoside, melting point 154°–156°C, $[\alpha]_D^{20} = -52.4°$ in methanol, is thus obtained.

EXAMPLE 2

Analogously to the description in Example 1, 4-(2,3-epoxy-propoxy)-phenyl-2,3,4,6-tetra-O-acetyl-β-D-glucopyranoside with isopropylamine gives 1-[p-(2,3,4,6-tetra-O-acetyl-β-D-glucopyranosidyloxy)-phenoxy]-2-hydroxy-3-isopropylamino-propane.

EXAMPLE 3

Analogously to the description in Example 1, 4-(2,3-epoxy-propoxy)-phenyl-2,4-O-isopropylidene-β-D-glucopyranoside with isopropylamine gives 1-[p-(2,4-O-isopropylidene-β-D-glucopyranosidyloxy)-phenoxy]-2-hydroxy-3-isopropylamino-propane.

EXAMPLE 4

Analogously to the description in Example 1, 4-(2,3-epoxy-propoxy)-phenyl-2,4-O-benzylidene-β-D-glucopyranoside with isopropylamine gives 1-[p-(2,4-O-benzylidene-β-D-gglucopyranosidyloxy)-phenoxy]-2-hydroxy-3-isopropylamino-propane.

EXAMPLE 5

Tablets containing 20 mg of active substance and having the following composition are prepared in the usual manner:

| Composition | |
|---|---|
| 1-[p-(β-D-Glucopyranosidyloxy)-phenoxy]-2-hydroxy-3-isopropylamino-propane | 20 mg |
| Wheat starch | 60 mg |
| Lactose | 50 mg |
| Colloidal silica | 5 mg |
| Talc | 9 mg |
| Magnesium stearate | 1 mg |
| | 145 mg |

Preparation

The 1-[p-(β-D-gulcopyranosidyloxy)-phenoxy]-2-hydroxy-3-isopropylamino-propane is mixed with a part of the wheat starch, with lactose and with colloidal silica and the mixture is forced through a sieve. A further part of the wheat starch is worked into a paste with a 5-fold quantity of water on a waterbath and the powder mixture is kneaded with this paste until a slightly plastic mass has been produced.

The plastic mass is forced through a sieve of approx. 3 mm mesh width and dried, and the resulting dry granules are again forced through a sieve. Thereafter, the residual wheat starch, talc and magnesium stearate are mixed in and the mixture is pressed to give tablets weighing 145 mg and having a breaking groove.

EXAMPLE 6 a. 27.2 g (0.1 mol) of hydroquinone-β-D-glucopyranoside and 250 ml of epichlorohydrin are dissolved in 1 liter of ethanol, 6.9 g (0.05 mol) of potassium carbonate are added and the mixture is heated for 6 hours under reflux. The precipitate which separates out is filtered off. The filtrate is concentrated in a waterpump vacuum. The residue is dissolved in ethanol whilst hot, and the solution is filtered. The filtrate is cooled and ether is added until the mixture begins to turn cloudy. The reaction product which hereupon precipitates in a crystalline form is filtered off and washed with ether. This gives 4-(2,3-epoxy-propoxy)-phenyl-β-D-glucopyranoside as a diastereomer mixture, melting point 154°–156°C, $[\alpha]_D^{20} = -52.4°$ in methanol.

b. 25 g of the diasteromer mixture are dissolved in 300 ml of methanol and heated for 6 hours with 18.5 g of isopropylamine to the reflux temperature. The reaction mixture is then concentrated completely by evaporation. The residue is dissolved in 35 ml of water and 11.6 g of cyclohexylsulphamic acid dissolved in acetone are added. Acetone is added to this solution until the mixture begins to turn cloudy. Hereupon, the reaction product begins to separate out in a crystalline form. To complete the crystallisation, the mixture is left to stand for 15 hours at 0°C. The crystals which have precipitated are filtered off and recrystallised three times from acetone-water. 10 g of the pure diastereomer of 1-[p-(β-D-glucopyranosidyloxy)-phenoxy]-3-isopropylamino-2R-propanol N-cyclohexylsulphamate dihydrate are obtained, $[\alpha]_D^{20}: -16.5° \pm 0.5°$ (C = 1.04% g/v in methanol).

The mother liquors obtained in the crystallisation process are combined and concentrated in a waterpump vacuum to give a syrup, which is dissolved in 50 ml of water. This solution is filtered through a column of 200 ml of Amberlite IRA-400 R (strongly basic ion exchanger with trimethylammonium groups [particle size 0.38–0.45 mm]). The column is washed with water until the base liberated has been eluted completely. The combined aqueous eluates are completely concentrated by evaporation in a waterpump vacuum and the product is recrystallised three times from methanol-isopropanol. The second diastereomer, namely 1-[p-(β-D-glucopyranosidyloxy)-phenoxy]-3-isopropylamino-(2S)-propanol, is obtained; melting point 157°–160°C/186°–189°C, $[\alpha]_D^{20} = -40° + 1°$, $[\alpha]_{Hg}^{20} = -138° \pm 1°$ (methanol, c = 1.008).

EXAMPLE 7 a. A solution of 9.4 g of 4-(2S,3-epoxypropoxy)-phenyl-β-D-glucopyranoside in 94 ml of ethanol and 46.7 ml of isopropylamine is warmed to 70°C for 45 minutes and is then freed from the solvent and excess amine in a waterpump vacuum. The crystalline residue is recrystallised from 230 ml of methanol, after which 4-(3-isopropylamino-2S-hydroxy-propoxy)-phenyl-β-D-glucopyranoside is obtained; melting point 186°–188°C; $[\alpha]_D^{20} = -46° \pm 1°$; $[\alpha]_{Hg}^{20} = -161° \pm 1°$ (methanol, c = 1.286).

b. 230 mg of N-cyclohexylsulphamic acid are added to a solution of 500 mg of 4-(3-isopropylamino-2S-hydroxy-propoxy)-phenyl-β-D-glucopyranoside in 10 ml of methanol, after standing for 30 minutes at about 25°C the mixture is freed from the solvent in a waterpump vacuum and the residue is dried in a high vacuum, after which the amorphous N-cyclohexylsulphamic acid salt of 4-(3-isopropylamino-2S-hydroxy-propoxy)-phenyl-β-D-glucopyranoside-is obtained. $[\alpha]_D^{20} = -40° \pm 1°$, $[\alpha]_{Hg}^{20} = -138° \pm 1°$ (methanol, c = 1.008).

4-(2S,3-Epoxypropoxy)-phenyl-β-glucopyranoside, used as the starting material, is prepared as follows:

c. A solution of 100 g of 4-hydroxyphenyl-β-D-glucopyranoside and 60.5 g of 1-O-benzyl-2S-anhydro-D-glycerol in 366 ml of 0.1 N sodium hydroxide solution and 740 ml of acetonitrile is boiled under reflux in a nitrogen atmosphere for 50 hours. The solvent is then distilled off in a waterpump vacuum and the residue is taken up in 1 liter of water. The product which has crystallised out is filtered off, recrystallised from 1 liter of water and dried, whereupon 4-(3-benzyloxy-2S-hydroxy-propoxy)-phenyl-β-D-glucopyranoside is obtained, melting point 146°–147°C; Rf value 0.45 on silica gel thin layer plates in the system methylene chloride-methanol, 3:1; $[\alpha]_D^{20} = -34° \pm 1°$ (methanol; c = 1.027).

d. 270 ml of acetic anhydride are added to a solution of 123 g of 4-(3-benzyloxy-2S-hydroxy-propoxy)-phenyl-β-D-glucopyranoside in 1,400 ml of pyridine whilst cooling with ice and the mixture is left to stand for 16 hours at about 25°C and is poured onto 3,000 ml of ice water. After standing for 2 hours, the crystalline product is filtered off, washed 3 times with 500 ml of water, dried and recrystallised from 700 ml of ethanol, after which 4-(2S-acetoxy-3-benzyloxy-propoxy)-phenyl-2,3,4,6-tetra-O-acetyl-β-D-glucopyranoside is obtained; melting point 93°–95°C; Rf value 0.37 on silica gel thin layer plates in the system methylene chloride-ethyl acetate, 85:15; $[\alpha]_D^{20} = -22° \pm 1°$ (chloroform, c = 0.967).

e. A solution of 144 g of 4-(2S-acetoxy-3-benzyloxy-propoxy)-phenyl-2,3,4,6-tetra-O-acetyl-β-D-glucopyranoside in 1,500 ml of methanol is hydrogenated with 14 g of 5% strength palladium-on-charcoal catalyst under normal pressure. The catalyst is filtered off and the solvent is distilled off in a waterpump vacuum. After recrystallisation from ether-petroleum ether, 4-(2S-acetoxy-3-hydroxy-propoxy)-phenyl-2,3,4,6-tetra-O-acetyl-β-D-glucopyranoside, melting point 103°–105°C, is obtained; Rf value 0.22 on silica gel thin layer plates in the system methylene chloride-ethyl acetate, 85:15; $[\alpha]_D^{20} = -29° \pm 1°$ (chloroform, c = 1.141).

f. 17.4 ml of methanesulphonic acid chloride are added dropwise over the course of one hour to a solution of 116 g of 4-(2S-acetoxy-3-hydroxy-propoxy)-phenyl-2,3,4,6-tetra-O-acetyl-β-D-glucopyranoside in 700 ml of pyridine whilst cooling with ice, and the mixture is left to stand for 5 hours at about 25°C. The reaction mixture is then poured onto 5 liters of ice water, whereupon the product crystallises out. The crystals are filtered off, thoroughly washed with water, dried and recrystallised from 800 ml of hot ethanol, whereupon 4-(2R-acetoxy-3-methanesulphonyloxy-propoxy)-phenyl-2,3,4,6-tetra-O-acetyl-β-D-glucopyranoside is obtained; melting point 110°–115°C; Rf value 0.20 on silica gel thin layer plates in the system methylene chlroide-ethyl acetate, 85:15; $[\alpha]_D^{20} = -28° \pm 1°$ (chloroform, c = 1.223).

g. 250 g of strongly basic anion exchange resin Dowex 1 (OH⁻), 50–100 mesh, which have been freshly regenerated and washed with absolute methanol, are added to a suspension of 103 g of 4-(2R-acetoxy-3-methanesulphonyloxy-propoxy)-phenyl-2,3,4,6-tetra-O-acetyl-β-D-glucopyranoside in 3 liters of absolute methanol and the mixture is stirred vigorously for 30 minutes at about 25°C. The anion exchanger is then filtered off and washed with 500 ml of methanol. The filtrate is concentrated to about 300 ml in a waterpump vacuum and 1 liter of ether is added, whilst stirring. The product which has crystallised out is filtered off and recrystallised from ethanol-ether, whereupon 4-(2S,3-epoxypropoxy)-phenyl-β-D-glucopyranoside is obtained; melting point 134°–136°C; Rf value 0.37 on silica gel thin layer plates in the system methylene chloride-methanol, 3:1; $[\alpha]_D^{20} = -44° \pm 1°$, $[\alpha]_{Hg}^{20} = -168° \pm 1°$ (methanol, c = 1.703).

EXAMPLE 8 a. 2.25 g of 1-(4-hydroxyphenoxy)-(2,S)-2-hydroxy-3-isopropylamino-propane, 3.3 g of hexamethyldisilazane and 20 ml of absolute dichloroethane are heated under reflux for 6 hours. The mixture is then evaporated in a waterpump vacuum and ultimately at 1 mmHg and 40°C bath temperature. The resulting syrupy residue is dissolved, together with 7.8 g of β-pentaacetylglucose, in 30 ml of dichloroethane, the solution is cooled to −10°C and a solution of 5.2 g of tin tetrachloride in 10 ml of dichloroethane is added dropwise at a rate such that the temperature does not rise above 0°C. After 4 hours, the reaction mixture is stirred into 200 ml of 5% strength sodium bicarbonate solution and the organic phase is separated from the resulting precipitate and from the aqueous phase, washed with water, adjusted to pH 5 with a mixture of equal volumes of concentrated hydrochloric acid and ethanol, dried over sodium sulphate and evaporated in a waterpump vacuum. 15 ml of acetone are added to the syrupy residue, followed by 15 ml of ethyl acetate after crystallisation has started, whereupon 4-(3-isopropylamino-(2,S)-2-hydroxy-propoxy)-phenyl-2,3,4,6-tetra-O-acetyl-β-D-glucopyranoside hydrochloride is obtained; melting point 256°–258°C, $[\alpha]_D^{20} = -23.5°$ in methanol.

The starting material is prepared as follows:

b. A few drops of pyridine are added to a melt, warmed to 120°C, of 100g of 5,6-anhydro-1,2-O-isopropylidine-α-D-glucofuranose and 100 g of hydroquinone monobenzyl ether whilst keeping the internal temperature below 140°C by external cooling with lukewarm water. After the exothermic reaction has subsided, the reaction mixture is additionally stirred for 30 minutes at 140°C and then cooled to 80°C, and 500 ml of methanol are added, followed by water until the mixture begins to turn cloudy. After standing for some hours at 0°C, the crystals which have precipitated are filtered off and recrystallised from methanol, whereupon 1,2-O-isopropylidene-6-O-(4-benzyloxyphenyl)-α-D-glucofuranose is obtained; melting point 99°–102°C; Rf value = 0.25 on silica gel thin layer plates in the system methylene chloride:methanol, 15:1.

c. 500 ml of water added dropwise, whilst stirring, to a solution, warmed to 70°C, of 127.3 g of 1,2,O-isopropylidene-6-O-(4-benzyloxy-phenyl-α-D-glucofuranose in 800 ml of glacial acetic acid, and the mixture is stirred for a further 14 hours at 70°C and is then evaporated to dryness in a waterpump vacuum. The crystalline residue is recrystallised from 1 liter of glacial acetic acid, whereupon 6-O-(4-benzyloxy-phenyl)-D-glucose is obtained; melting point 164°–168°C; Rf value = 0.61 on silica gel thin layer plates, using methanol; $[\alpha]_D^{20} = -62° \pm 1°$ (methanol, c = 0.985).

d. 64 g of sodium meta-periodate are added in portions, over the course of 15 minutes, to a suspension of 36.2 g of the 6-(4-benzyloxyphenyl)-D-glucose obtained, in a mixture of 600 ml of methanol, 10 ml of glacial acetic acid and 60 ml of water, whilst cooling externally and stirring the mixture; thereafter, the mixture is stirred for 20 hours at about 25°C. Insoluble material is filtered off, the filtrate is evaporated to dryness, the residue is taken up in chloroform, this solution is washed with water and dried over magnesium sulphate, and the solvent is evaporated off in a waterpump vacuum. The residue is dissolved in 150 ml of methanol and the solution is added dropwise, over the course of 45 minutes, to a solution, cooled to −5°C, of 3.8 g of sodium borohydride in 150 ml of methanol and 40 ml of water. After standing for a further 15 hours at about 25°C, the reaction mixture is evaporated to dryness the residue is taken up in chloroform, the solution is washed with ice-cold 2N hydrochloric acid and water and after drying over magnesium sulphate the solvent is evaporated off in a waterpump vacuum. The residue is recrystallised from chloroform, whereupon 1-(4-benzyloxyphenoxy-2S,3-dihydroxy-propane is obtained; melting point 134°–138°C; Rf value = 0.32 on silica gel thin layer plates in the system methylene chloride:methanol, 15:1.

e. A solution of 5.7 g of p-tosyl chloride in 30 ml of pyridine is added dropwise over the course of 4 hours to a solution, cooled to −10°C, of 8.2 g of the 1-(4-benzyloxy-phenoxy)-2S,3-dihydroxy-propane obtained, in 20 ml of pyridine, whilst stirring and excluding moisture, and the mixture is left to stand for 16 hours at about 25°C. The reaction mixture is then diluted with chloroform and water and the organic phase is separated off, washed with ice-cold 2N hydrochloric acid, with water, with a saturated sodium bicarbonate solution and finally again with water, dried over magnesium sulphate and freed from the solvent. The residue is purified by column chromatography on 250 g of silica gel, using a 19:1 mixture of methylene chloride and ethyl acetate, and the product is recrystallised from an ethyl acetate/petroleum ether mixture, whereupon 1-(4-benzyloxy-phenoxy)-2R-hydroxy-3-p-tosyloxy-propane is obtained; melting point 70°–74°C; Rf value = 0.36 on silica gel thin layer plates in the system methylene chloride:ethyl acetate, 19:1; $[\alpha]_D^{20} = 11 \pm 1°$ (chloroform, c = 1.631).

f. A solution of 3.8 g of 1-(4-benzyloxy-phenoxy)-2R-hydroxy-3-p-tosyloxy-propane in 40 ml of ethanol and 4 ml of isopropylamine is kept for 30 hours at a temperature of 50°C and is then evaporated to dryness. The residue is taken up in methylene chloride, the solution is washed with 2N sodium hydroxide solution and then with water and dried over magnesium sulphate and the solvent is distilled off, whereupon 1-isopropylamino-2S-hydroxy-3-(4-benzyloxy-phenoxy)-propane is obtained, which is recrystallised from methylene chloride/petroleum ether; melting point 91°–93°C.

This compound is dissolved in a little ethanol and alcoholic hydrochloric acid is added to bring the pH to 4; ether is then added until the mixture turns cloudy. After cooling, 1-isopropylamino-2S-hydroxy-3-(4-benzyloxyphenoxy)-propane hydrochloride crystallises out and is filtered off and dried; melting point 161°–163°C; $[\alpha]_D^{20} = -19° \pm 1°$; $[\alpha]_{Hg}^{20} = -57° \pm 1°$ (methanol, c = 4.903).

g. A solution of 1.6 g of 1-isopropylamino-2S-hydroxy-3-(4-benzyloxy-phenoxy)-propane hydrochloride in 160 ml of ethanol is hydrogenated with 0.2 g of 5% strength palladium-on-charcoal, under normal pressure. After the calculated amount of hydrogen has been taken up, the catalyst is filtered off and the solution is evaporated to dryness. The residue is dissolved in 45.6 ml of 0.1 N sodium hydroxide solution and the solution is extracted with ethyl acetate. The organic phase is dried over magnesium sulphate and evaporated and the residue is recrystallised from ethyl acetate, whereupon 1-isopropylamino-2S-hydroxy-3-(4-hydroxyphenoxy)-propane is obtained; melting point 127°–128°C; $[\alpha]_D^{20} = -1° \pm 1°$; $[\alpha]_{Hg}^{20} = +2° \pm 1°$ (methanol, c = 0.940).

9.1 ml of a 4% strength solution of fumaric acid in methanol are added to a solution of 0.7 g of the 1-isopropylamino-2S-hydroxy-3-(4-hydroxy-phenoxy)-propane obtained, in 5 ml of methanol. Ether is added to this mixture until it turns cloudy, and the solution is cooled. The resulting crystals are filtered off and dried, and consist of 1-isopropylamino-2S-hydroxy-3-(4-hydroxy-phenoxy)-propane. ½ fumarate; melting point 209°–211°C; $[\alpha]_D^{20} = -23° \pm 1°$; $[\alpha]_{Hg}^{20} = -68° \pm 1°$, (methanol, c = 1.061).

EXAMPLE 9

1.0 g of 4-(3-isopropylamino-(2,S)-2-hydroxy-propoxy)-phenyl-2,3,4,6-tetra-O-acetyl-β-D-glucopyranoside hydrochloride is dissolved in 50 ml of methanol which has been saturated with ammonia at 0°C, and the mixture is left to stand at room temperature for 7 hours. It is then concentrated completely by evaporation in a waterpump vacuum and the residue is successively triturated with 10 ml of ethyl acetate and with 10 ml of isopropanol, and filtered off. After recrystallisation from methanol, 4-(3-isopropylamino-(2,S)-2-hydroxy-propoxy)-phenyl-β-D-glucopyranoside hydrochloride is obtained; melting point 168°–170°C, $[\alpha]_D^{20} = -40.8°$ in methanol.

EXAMPLE 10

Tablets containing 20 mg of active substance are prepared in the usual manner, to have the following composition:

| Composition | |
|---|---|
| 1-[p-(β-D-glucopyranosidyloxy)-phenoxy]-2S-hydroxy-3-isopropylamino-propane | 20 mg |
| Wheat starch | 60 mg |
| Lactose | 50 mg |
| Colloidal silica | 5 mg |
| Talc | 9 mg |
| Magnesium stearate | 1 mg |
| | 145 mg |

Manufacture

The 1-[p-(β-D-glucopyranosidyloxy)-phenoxy]-(2,S)-2-hydroxy-3-isopropylamino-propane is mixed with a part of the wheat starch, with lactose and with colloidal silica and the mixture is forced through a sieve. A further part of the wheat starch is worked into a paste with a 5-fold amount of water on a water bath and the powder mixture is kneaded with this paste until a slightly plastic mass has been produced.

The plastic mass is forced through a sieve of approx. 3 mm mesh width and dried and the resulting dry granules are again forced through a sieve. Thereafter, the remaining wheat starch, talc and magnesium stearate are admixed and the mixture is pressed to give tablets weighing 145 mg and having a breaking groove.

We claim:

1. A compound which is a 1-phenoxy-2-hydroxy-3-amino-propane of the formula

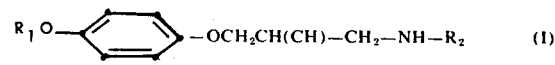

(1)

wherein $R_1$ represents 1-glucopyranosidyl, 2,3,4,6-tetra-O-alkanoylated 1-glucopyranosidyl, the alkanoyl radical of which having up to four carbon atoms, or 2,4-O,O-alkylidene substituted 1-glucopyranosidyl, the alkylidene radical of which having up to four carbon atoms, or 2,4-O-benzylidene substituted 1-glucopyranosidyl, $R_2$ is isopropyl, tert.-butyl, α-methylphenethyl or 1-methyl-3-phenyl-propyl, or a pharmaceutically acceptable salt thereof.

2. A compound as claimed in claim 1, wherein $R_1$ represents 1-glucopyranosidyl, 2,3,4,6-tetra-O-acetyl-1-glucopyranosidyl, 2,4-O-isopropylidene-1-glucopyranosidyl or 2,4-O-benzlidene-1-glucopyranosidyl, and $R_2$ is isopropyl, tert.-butyl or α-methylphenethyl or 1-methyl-3-phenyl-propyl, or a pharmaceutically acceptable salt thereof.

3. A compound as claimed in claim 1, wherein $R_1$ is 1-glucopyranosidyl and $R_2$ is isopropyl or tert.-butyl, or a pharmaceutically acceptable salt thereof.

4. A compound as claimed in claim 1 being 1-[p-(β-D-glucopyranosidyloxy)-phenoxy]-2-hydroxy-3-isopropylamino-propane, or a pharmaceutically acceptable salt thereof.

5. A compound as claimed in claim 1 being an optically active 1-phenoxy-2-hydroxy-3-aminopropane, having the S-configuration, of the formula I, wherein $R_1$ is O-acetyl-1-glucopyramosidyl or O-benzoyl-1-glucopyranosidyl and $R_2$ is isopropyl, tert.-butyl or α-methylphenethyl or 1-methyl-3-phenyl-propyl, or a pharmaceutically acceptable salt thereof.

6. A compound as claimed in claim 1 being 1-[p-(β-glucopyranosidyloxy)-phenoxy]-2S-hydroxy-3-isopropylaminio-propane, or a pharmaceutically acceptable salt thereof.

7. The N-cyclohexylsulphamic acid salt of the compound of claim 6.

8. The hydrochloride salt of the compound of claim 6.

9. A compound as claimed in claim 1 being 4-(3-Isopropylamino-2S-hydroxy-propoxy)-phenyl-2,3,4,6-tetra-O-acetyl-β-D-glucopyranoside, or a pharmaceutically acceptable salt thereof.

10. The hydrochloride salt of the compound of claim 9.

11. A compound as claimed in claim 1 being an optically active 1-phenoxy-2-hydroxy-3-aminopropane having the S-configuration of the formula I, wherein $R_1$ represents 1-glucopyranosidyl, 2,3,4,6-tetra-O-alkanoylated 1-glucopyranosidyl, the alkanoyl radical of which having up to four carbon atoms, or 2,4-O,O-alkylidene substituted 1-glucopyranosidyl, the alkylidene radical of which having up to four carbon atoms, or 2,4-O,O-benzylidene substituted 1-glucopyranosidyl, $R_2$ is isopropyl, tert.-butyl, α-methylphenethyl or 1-methyl-3-phenyl-propyl, or a pharmaceutically acceptable salt thereof.

* * * * *